United States Patent [19]

Stapler et al.

[11] Patent Number: 5,286,496
[45] Date of Patent: Feb. 15, 1994

[54] BREATH PROTECTION MICROCAPSULES

[75] Inventors: Judith H. Stapler, Wilmington; Mary Ann Hunter, Cincinnati, both of Ohio

[73] Assignee: The Procter & Gamble Company, Cincinnati, Ohio

[21] Appl. No.: 3,080

[22] Filed: Jan. 11, 1993

Related U.S. Application Data

[63] Continuation-in-part of Ser. No. 805,432, Dec. 11, 1991, abandoned.

[51] Int. Cl.$^5$ .................... A61K 9/50; A61K 9/16; A61K 9/68
[52] U.S. Cl. .................... 424/490; 424/48; 424/49; 424/58; 424/435; 424/440; 424/492; 514/948; 514/963
[58] Field of Search .................... 424/48, 49, 58, 435, 424/440, 490, 492; 514/948, 963

[56] References Cited

U.S. PATENT DOCUMENTS

| | | | |
|---|---|---|---|
| 2,311,923 | 2/1943 | Lautmann | 167/82 |
| 2,446,792 | 8/1948 | Shelton et al. | 260/295 |
| 3,431,208 | 3/1969 | Bailey | 252/106 |
| 3,832,460 | 8/1974 | Kosti | 424/54 |
| 3,911,099 | 10/1975 | DeFoney et al. | 424/28 |
| 3,957,964 | 5/1976 | Grimm, III | 424/10 |
| 3,962,383 | 6/1976 | Hagiwara et al. | 264/4 |
| 4,039,653 | 8/1977 | DeFoney et al. | 424/16 |
| 4,071,614 | 1/1978 | Grimm, III | 424/49 |
| 4,169,885 | 10/1979 | Raaf et al. | 424/16 |
| 4,196,189 | 4/1980 | Raaf et al. | 424/37 |
| 4,251,195 | 2/1981 | Suzuki et al. | 425/6 |
| 4,260,596 | 10/1981 | Mackles | 424/14 |
| 4,312,889 | 1/1982 | Melsheimer | 426/86 |
| 4,329,333 | 5/1982 | Barr | 424/19 |
| 4,409,202 | 10/1983 | Witzel et al. | 424/49 |
| 4,422,985 | 12/1983 | Morishita et al. | 264/4.4 |
| 4,426,337 | 1/1984 | Suzuki et al. | 264/4 |
| 4,481,157 | 11/1984 | Morishita et al. | 264/4.1 |
| 4,597,959 | 7/1986 | Barr | 424/19 |
| 4,690,816 | 9/1987 | Hata et al. | 424/456 |
| 4,695,466 | 9/1987 | Morishita et al. | 424/456 |
| 4,710,384 | 12/1987 | Rotman | 424/465 |
| 4,749,575 | 6/1988 | Rotman | 424/441 |
| 4,762,719 | 8/1988 | Forester | 424/440 |
| 4,765,984 | 8/1988 | Vellekoop et al. | 424/441 |
| 4,800,087 | 1/1989 | Mehta | 424/497 |
| 4,847,090 | 7/1989 | Dell Posta et al. | 424/440 |
| 4,857,335 | 8/1989 | Bohm | 424/455 |
| 4,861,268 | 8/1989 | Garay et al. | 433/229 |
| 4,906,488 | 3/1990 | Pera | 426/573 |
| 4,952,402 | 8/1990 | Sparks et al. | 424/419 |
| 5,004,595 | 4/1991 | Cherukuri et al. | 424/48 |
| 5,008,106 | 4/1991 | Merianos et al. | 424/80 |
| 5,013,557 | 5/1991 | Tai | 424/493 |
| 5,064,650 | 11/1991 | Lew | 424/435 |
| 5,084,278 | 1/1992 | Mehta | 424/441 |
| 5,098,725 | 3/1992 | Rotman et al. | 426/98 |
| 5,164,195 | 11/1992 | Lew | 424/490 |
| 5,169,631 | 12/1992 | Rase et al. | 424/401 |

FOREIGN PATENT DOCUMENTS

| | | |
|---|---|---|
| 0022662 | 1/1981 | European Pat. Off. |
| 0273823 | 7/1988 | European Pat. Off. |
| 0332175 | 9/1989 | European Pat. Off. |
| 0423002 | 4/1991 | European Pat. Off. |
| 2051483 | 4/1971 | France |
| 2570604 | 3/1986 | France |
| 2643261 | 8/1990 | France |
| 1060258 | 3/1967 | United Kingdom |
| 2210889 | 6/1989 | United Kingdom |
| 89/10117 | 11/1989 | World Int. Prop. O. |
| 90/02655 | 3/1990 | World Int. Prop. O. |
| 91/06292 | 5/1991 | World Int. Prop. O. |

*Primary Examiner*—Shep K. Rose
*Attorney, Agent, or Firm*—D. C. Mohl; K. W. Zerby; J. C. Rasser

[57] ABSTRACT

The present invention relates to oral compositions in the form of microcapsules which reduce oral bacteria and provide long lasting breath protection.

11 Claims, No Drawings

BREATH PROTECTION MICROCAPSULES

CROSS REFERENCE TO RELATED APPLICATION

This is a continuation-in-part application of application Ser. No. 805,432, filed Dec. 11, 1991, now abandoned.

TECHNICAL FIELD

The present invention relates to oral compositions in the form of microcapsules which reduce oral bacteria and provide long lasting breath protection.

BACKGROUND OF THE INVENTION

The use of breath control compositions such as breath mints, mouthwashes, chewing gums, etc. is widespread in most of the developed countries of the world. Another form which has been used are microcapsules containing a flavorant or other breath protection agent. These executions have acceptance due not only to their usefulness away from a place to expectorate mouthwashes but also due to the fact that they can be swallowed when the user does not need any more of the actives or doesn't want the microcapsule in the mouth any longer.

Although microcapsules have been used, there are problems associated with incorporating certain breath protection agents/antimicrobials into the core. Oftentimes the wall of the microcapsule may develop imperfections and cause loss of the contents prematurely. Additionally, the actives may not be easily solubilized in the materials usually present in the core.

The prior art discloses a variety of means for providing breath protection and reducing oral bacteria. Included among such means are sprays disclosed in U.S. Pat. No. 3,431,208, Mar. 4, 1969 to Bailey. Particles containing an adhesive member are disclosed in U.S. Pat. No. 3,911,099, Oct. 7, 1975 to Den Foney et al. Another form is a mouthwash concentrate in a unit dosage cup as disclosed in U.S. Pat. No. 4,312,889, Jan. 26, 1982 to Melsheimer. All of these references are incorporated herein by reference.

The present inventors have found that by incorporating the breath control/antimicrobial actives into the core of the microcapsule along with organic diluents, problems associated with other microcapsule executions can be avoided.

It is therefore an object of the present invention to provide improved microcapsules.

It is another object of the present invention to provide microcapsules which provide improved breath control and reduce oral bacteria.

It is still another object of the present invention to provide improved methods of providing breath control and reducing oral bacteria.

These and other objects will become more apparent from the detailed description which follows.

All percentages and ratios used herein are by weight unless otherwise specified. Additionally, all measurements are made at 25° C. unless otherwise specified.

SUMMARY OF THE INVENTION

The present invention in one of its aspects relates to microcapsules which contain breath control actives/antimicrobials in the core of the microcapsule along with an organic diluent as well as in the shell of the microcapsule.

DETAILED DESCRIPTION OF THE INVENTION

The essential as well as optional components of the capsules of the present invention are described in the following paragraphs.

Capsule Shell Material

The shell material of the microcapsules of the present invention can be any materials which are suitable for ingestion as well as retention in the oral cavity. Materials which are suitable include gelatin, polyvinyl alcohols, waxes, gums, sucrose esters and sugar candy type materials used in cough drops and mints, for example.

The shell material is used to form any of a wide variety of shapes such as spheres, oblong shapes, disks, puffed squares and cylinders. The shell thickness is preferably in the range of about 30 um to about 2 mm, preferably from about 70 um to about 110 um. If the microcapsules are spherical, the particle diameter is generally in the range of from about 2 mm to about 9 mm, preferably from about 3 mm to about 7 mm.

Breath Control Agents/Antimicrobials Present in the Core and in the Shell Material The breath control agents used in the cores of the microcapsules include quaternary ammonium salts such as pyridinium salts (e.g., cetyl pyridinium chloride), domiphen bromide, other cationic materials such as chlorhexidine salts, zinc salts and copper salts. Other organic agents such as triclosan and other noncationic water insoluble agents are also useful herein. Such materials are disclosed in U.S. Pat. 5,043,154, Aug. 27, 1991, incorporated by reference herein.

These breath control/antimicrobial agents are used in an amount of from about 0.001% to about 2%, preferably from about 0.005% to about 1% of the total core contents.

Dispersed within the shell material may be the same agents at the same concentrations.

Diluents for Use in Microcapsule Core

The solubilizing agent for the breath control/antimicrobial agents used in the cores of the present microcapsules can be any of a number of materials. Preferred are oils such as corn, olive, rapeseed, sesame, peanut or sunflower. Other preferred materials are triglycerides such as Captex 300 and polyethylene glycols such as PEG 400. These are used in an amount of from about 20% to about 80%, preferably from about 35% to about 70% of the total capsule weight.

Additional Agents Suitable for Use in the Core of Capsule

The core of the microcapsules of this invention may contain any number of additional materials to provide additional efficacy and/or sensory perceptions. Such agents may include flavoring agents such as thymol, eucalyptol, menthol, methyl salicylate or witch hazel. These agents are used in an amount of from about 0.1% to about 25%, preferably from about 10% to about 15% of the total capsule weight.

In addition, a variety of sweetening agents such as sugars, corn syrups, saccharin or aspartame may also be included in the core. These agents are used in an amount of from about 0.1% to about 5%, preferably from about 0.35% to about 0.5% of the total capsule weight.

Method of Manufacture

The capsules of the present invention can be made using a variety of techniques. One method is described after the following examples.

Industrial Applicability

The capsules of the present invention are used by placing the capsules into the mouth and retaining them therein for a period sufficient to provide the desired effect.

The following examples further describe and demonstrate preferred embodiments within the scope of the present invention. The examples are given solely for the purposes of illustration and are not to be construed as illustrative of limitations of this invention. Many variations thereof are possible without departing from the invention's spirit and scope.

EXAMPLES 1–4

The following compositions/capsules are representative of the present invention.

| Component | Weight % | | | | |
|---|---|---|---|---|---|
|  | 1 | 2 | 3 | 4 | 5 |
| Gelatin | 12.578 | 12.328 | 12.578 | 17.578 | 10.360 |
| Sorbitol Solution (70% Aqueous) | 2.046 | 2.05 | 2.046 | 2.046 | 2.590 |
| Saccharin | 0.372 | 0.500 | 0.372 | 0.450 | 0.538 |
| FD & C Blue #1 | 0.002 | 0.002 | 0.002 | — | 0.013 |
| FD & C Yellow #5 | 0.002 | — | 0.002 | 0.004 | — |
| Captex 300[1] | 72.140 | 70.00 | 71.925 | 66.142 | 3.801 |
| Flavor | 12.750 | 15.00 | 12.75 | 13.500 | 5.986 |
| Cetyl Pyridinium[2] Chloride | 0.100 | — | — | — | 0.133 |
| Domiphen Bromide | 0.010 | — | — | — | 0.013 |
| Chlorhexidine | — | 0.12 | — | — | — |
| ZnCl$_2$ | — | — | 0.025 | — | — |
| Sodium Lauryl Sulfate | — | — | 0.300 | — | — |
| Triclosan | — | — | — | 0.28 | — |
| Polyethylene glycol 400 | — | — | — | — | 35.082 |
| Sucrose Acetate Isobutyrate | — | — | — | — | 38.846 |
| Water | — | — | — | — | 2.636 |

[1]Captex 300 is a triglyceride supplied by Capitol City Product, Columbus, Ohio.
[2]This amount includes that in the gelatin shell as well as in the core.

The above compositions are prepared by mixing the components of the core in one container and the components of the shell(s) in another container. The shell(s) materials are heated to provide a fluid medium. The core and shell(s) materials are then pumped separately to a two or three fluid nozzle submerged in an organic carrier medium. The capsules formed are allowed to cool and stiffen. They are then denatured and separated for further handling.

In the above compositions any of a wide variety of other shell materials, breath control agents, sweeteners as well as other components may be used in place of or in combination with the components listed above.

What is claimed is:

1. Microcapsules adapted to be placed and retained in the mouth, and which are suitable for providing breath protection comprising [a] a core, or center fill, into which it may not be possible to easily incorporate breath control actives, which core or center fill includes from about 20% to about 80% of the total capsule weight of oil, triglyceride or polyethylene glycol core diluent, said core containing from about 0.1% to about 25% of the total capsule weight of flavoring agents providing additional efficacy and/or sensory perceptions, and [b] a shell material, surrounding said core or center fill, suitable for retention in the oral cavity as well as for ingestion, and disposed within said shell material, from about 0.001% to about 2% of the total weight of the capsule, one or more breath control actives said microcapsules not being incorporated into breath mints, mouthwashes, chewing gums, or other breath control or oral hygiene compositions, said [a] core or center fill also containing breath control actives.

2. Microcapsules according to claim 1 wherein the shell material is selected from the group consisting of polyvinyl alcohol, gelatin, waxes, gums and sugar candies.

3. Microcapsules according to claim 2 wherein the microcapsule is in the form of a sphere, oblong, disk, a puffed square, or a cylinder and the breath control agent is a quaternary ammonium salt.

4. Microcapsules according to claim 3 wherein the microcapsules are in the form of spheres.

5. Microcapsules according to claim 4 wherein the microcapsules are from about 2 mm to about 9 mm in diameter and the shell wall thickness is from about 30 um to about 2 mm.

6. Microcapsules according to claim 5 wherein the shell material is gelatin.

7. Microcapsules according to claim 6 wherein the microcapsules are made using a three fluid nozzle.

8. A method of reducing oral bacteria or breath odor in the mouth wherein capsules according to claim 1 are placed in the mouth of a human or lower animal in need of reducing breath odor or bacteria and left therein for a time sufficient to provide a benefit.

9. A method according to claim 7 wherein the microcapsule shell is made of gelatin.

10. A method according to claim 8 wherein the breath control/antimicrobial active is selected from the group consisting of cetyl pyridinium chloride, domiphen bromide and mixtures thereof.

11. A method according to claim 9 wherein the microcapsule is in the form of a sphere.

* * * * *